(12) United States Patent  
Tung et al.

(10) Patent No.: US 8,969,593 B2  
(45) Date of Patent: Mar. 3, 2015

(54) ORGANIC DYES AND PHOTOELECTRIC CONVERSION DEVICES

(75) Inventors: Yung-Liang Tung, Hualien County (TW); Jia-Yin Wu, Taichung (TW); Jen-An Chen, Miaoli County (TW); Hsin-Yi Hsu, Miaoli County (TW); Chun-Guey Wu, Hualien (TW); Min-Fong Jhong, Zhonghe (TW); Song-Yeu Tsai, Taipei (TW)

(73) Assignee: Industrial Technology Research Institute, Hsinchu County (TW)

( * ) Notice: Subject to any disclaimer, the term of this patent is extended or adjusted under 35 U.S.C. 154(b) by 417 days.

(21) Appl. No.: 12/650,881

(22) Filed: Dec. 31, 2009

(65) Prior Publication Data

US 2010/0292488 A1 Nov. 18, 2010

(30) Foreign Application Priority Data

May 15, 2009 (TW) ............... 98116139 A

(51) Int. Cl.
C07D 495/04 (2006.01)
C07D 495/14 (2006.01)
(Continued)

(52) U.S. Cl.
CPC .......... *H01L 51/0074* (2013.01); *C07D 495/04* (2013.01); *C07D 495/14* (2013.01); *C07D 519/00* (2013.01); *Y02E 10/542* (2013.01)
USPC ............... 549/48; 429/111; 136/263

(58) Field of Classification Search
CPC .... C07D 495/04; C07D 495/14; H01L 31/00; H01L 51/0074
USPC ............... 549/48; 429/111; 136/263
See application file for complete search history.

(56) References Cited

U.S. PATENT DOCUMENTS

2006/0130249 A1* 6/2006 Ikeda et al. .......... 8/550
2007/0017571 A1* 1/2007 Gaudiana et al. ....... 136/263
(Continued)

FOREIGN PATENT DOCUMENTS

CN 101240117 * 8/2008
CN 101407639 * 4/2009
(Continued)

OTHER PUBLICATIONS

Thomas et. al. "2,3-Disubstituted Thiophene-Based Organic Dyes for Solar Cells" Chemistry of Materials 2008, 20, 1830-1840.*
Xu et. al. "Energy-Level and Molecular Engineering of Organic D-π-A Sensitizers in Dye-Sensitized Solar Cells" J. Phys. Chem. C 2008, 112, 19770-19776.*

Wang et al., "A High-Light-Harvesting-Efficiency Coumarin Dye for Stable Dye-Sensitized Solar Cells", Adv. Mater., 2007, 19, 1138-1141.
(Continued)

*Primary Examiner* — David K O Dell
(74) *Attorney, Agent, or Firm* — Pai Patent & Trademark Law Firm; Chao-Chang David Pai

(57) ABSTRACT

Organic dyes and photoelectric conversion devices are provided. The Organic dye has the structure represented by formula (I), wherein, n is an integral of 2-11; the plurality of X is independent and elected from the group consisting of

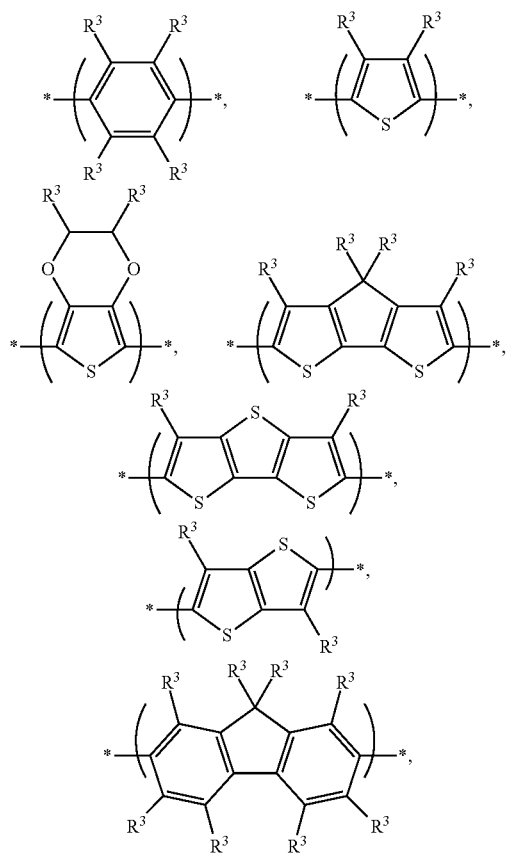

and combinations thereof; R, $R^1$, and $R^2$ comprise hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group, or $R^1$ is connected to $R^2$ to form a ring having 5-14 members; $R^3$ comprise hydrogen, halogen, nitro group, amino group, $C_{1-18}$ alkyl group, $C_{1-18}$ alkoxy group, $C_{1-18}$ sulfanyl group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; and Z is hydrogen, alkali metal, or quaternary ammonium salt.

7 Claims, 1 Drawing Sheet

(51) Int. Cl.
*H01L 31/00* (2006.01)
*H01L 51/00* (2006.01)
*C07D 519/00* (2006.01)

(56) References Cited

U.S. PATENT DOCUMENTS

| | | | |
|---|---|---|---|
| 2007/0073052 A1 | 3/2007 | Velusamy et al. | |
| 2007/0267055 A1* | 11/2007 | Gaudiana et al. | 136/244 |
| 2011/0041907 A1* | 2/2011 | Xu et al. | 136/256 |

FOREIGN PATENT DOCUMENTS

| | | | |
|---|---|---|---|
| CN | 101407639 A | | 4/2009 |
| CN | 101429346 A | | 5/2009 |
| JP | 2004-292742 A | | 10/2004 |
| JP | 2009-212035 A | | 9/2009 |
| JP | 2009-266633 A | | 11/2009 |
| TW | 200531593 | | 9/2005 |
| WO | 2004-082061 A1 | | 9/2004 |
| WO | 2007-007671 A1 | | 1/2007 |
| WO | 2007-100033 A1 | | 9/2007 |
| WO | 2008-147070 A2 | | 12/2008 |
| WO | 2009-051390 A2 | | 4/2009 |
| WO | 2009-098643 A2 | | 8/2009 |
| WO | 2010-002154 A2 | | 1/2010 |

OTHER PUBLICATIONS

Koumura et al., "Alkyl-Functionalized Organic Dyes for Efficient Molecular Photovoltaics", J. Am. Chem. Soc., 2006, 128, 14256-14257.

Kim et al., "Molecular Engineering of Organic Sensitizers for Solar Cell Applications", J. Am. Chem. Soc., 2006, 128, 16701-16707.

Horiuchi et al., "High Efficiency of Dye-Sensitized Solar Cells Based on Metal-Free Indoline Dyes", J. Am. Chem. Soc., 2004, 126, 12218-12219.

Hwang et al., "A highly efficient organic sensitizer for dye-sensitized solar cells", Chem. Commun., 2007, 4887-4889.

Notice of Allowance issued by the Japan Patent Office on Jul. 2, 2013, regarding the above-referenced application's counterpart application in Japan (Application No. 2010-112235).

Examination opinion issued by the Taiwan Intellectual Property Office on Aug. 15, 2012, for the above-referenced application's counterpart application in Taiwan (Application No. 098116139).

Li et al., "Dye-Sensitized Solar Cells Based on Organic Sensitizers with Different Conjugated Linkers: Furan, Bifuran, Thiophene, Bithiophene, Selenophene, and Biselenophene", J. Phys. Chem. C 2009, 113, 7469-7479.

Office Action (Notice of First examination opinion) issued by the China Intellectual Property Office on Aug. 31, 2012, for the above-referenced application's counterpart application in China (Application No. 200910142486.1).

Office Action (Notice of Reasons for Refusal) issued by the Japan Patent Office on Sep. 25, 2012, regarding the above-referenced application's counterpart application in Japan (Application No. 2010-112235).

Zhang et al., "Employ a Bisthienothiophene Linker to Construct an Organic Chromophore for Efficient and Stable Dye-Sensitized Solar Cells", Energy & Environ. Sci., 2009, 2, 92-95.

Li et al., "Dye-Sensitized Solar Cells Based on Organic Sensitizers with Different Conjugated Linkers: Furan, Bifuran, Thiophene, Bithiophene, Selenophene, and Biselenophene", J. Phys. Chem. C, 2009, 113, 7469-7479.

Yen et al., "Pyrrole-Based Organic Dyes for Dye-Sensitized Solar Cells", J. Phys. Chem. C., 2008, 112, 12557-12567.

Thomas et al., "2,3-Disubstituted Thiophene-Based Organic Dyes for Solar Cells", Chem., Mater., 2008, 20, 1830-1840.

* cited by examiner

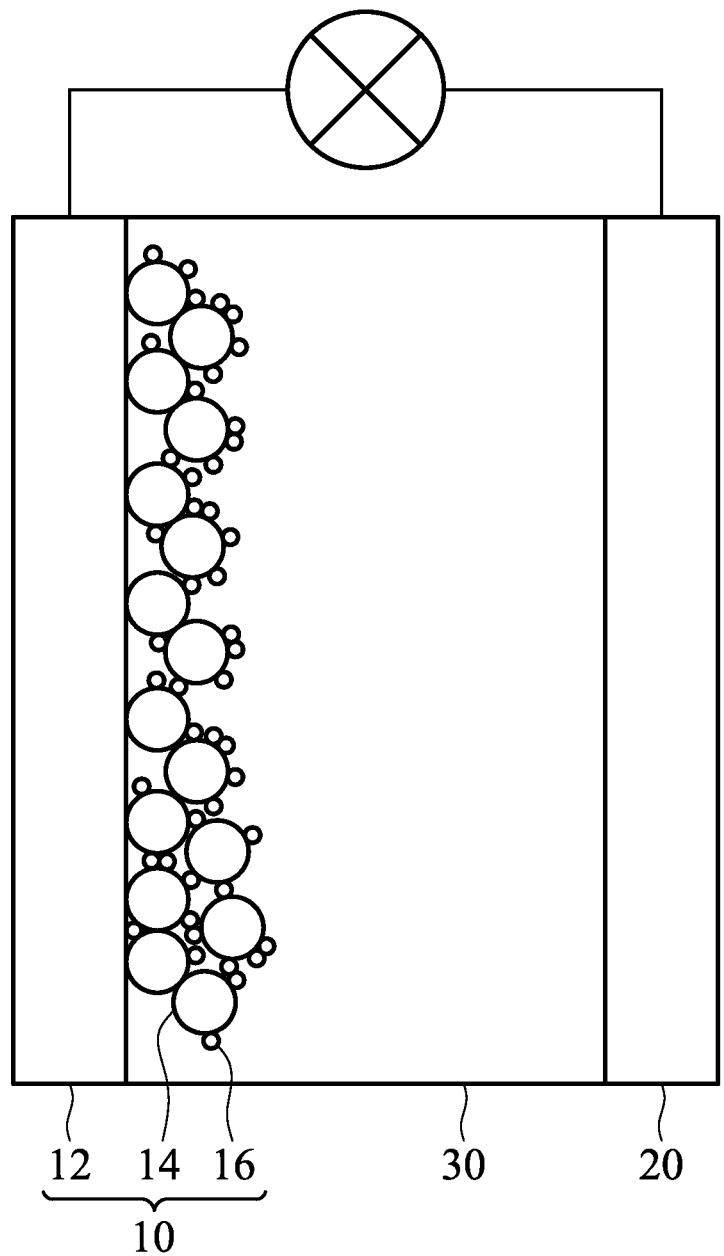

ORGANIC DYES AND PHOTOELECTRIC CONVERSION DEVICES

CROSS REFERENCE TO RELATED APPLICATIONS

This application is based upon and claims the benefit of priority from the prior Taiwan Patent Application No. 98116139, filed on May 15, 2009, the entire contents of which are incorporated herein by reference.

BACKGROUND OF THE INVENTION

1. Field of the Invention

The invention relates to an organic dye and, more particularly, to an organic dye used in photoelectric conversion devices.

2. Description of the Related Art

The demand for energy conservation triggered the search for alternate renewable energy sources. Recently, Gratzel and O'Regan have proposed a new type of solar cell known as a dye-sensitized solar cell (DSSC), which they claimed to be more efficient than other commercially available solar cells. The proposal has drawn much interest from solar cell researchers in academia and industry. Typically a dye-sensitized solar cell is constituted with four parts including an anode/cathode for providing a channel for current flow, a metal oxide (generally $TiO_2$) semiconductor for accepting and transporting electrons, a photosensitizer, and an electrolyte for transporting holes. The materials and the junctions of the four parts in the dye-sensitized solar cell play important roles for efficiency of the cell. Most particularly, the photosensitizer (or dye) is critical in determining the efficiency of the dye-sensitized solar cell. Accordingly, it is essential to identify a dye that can provide good efficiency for the dye-sensitized solar cell.

Currently, in order to yield devices high in conversion efficiency, a ruthenium based complex (such as N3 dye(cis-dithiocyanato-bis(4,4'-dicarboxy-2,2'-bipyridine) ruthenium)) is used as a sensitizing dye. However, costs of the dye itself are high, and further problems remain also in the supply thereof. Due to the high absorption coefficient, various structures, and accessibility of organic compounds, the Attempts wherein an organic dye for replacing is used as a sensitizing dye have already been made. It is well known that having high absorption coefficient is one of the most important parameters for being a good photosensitizer.

However, currently, no substitute organic dye has replaced the ruthenium based complex due to low conversion efficiency, and stability and durability issues of devices using the same. There is, therefore, still a need for an organic dye with high absorption coefficient and high conversion efficiency that may be employed in photoelectric conversion devices.

BRIEF SUMMARY OF THE INVENTION

The invention discloses organic dyes have an end of a diphenylamine moiety serving as a donor and another end of a CN—COOZ moiety (Z is hydrogen, alkali metal, or quaternary ammonium salt) serving as an acceptor, wherein the both ends are linked by a plurality of conjugated moiety serving as spacer.

An exemplary embodiment of an organic dye has a Formula (I), of:

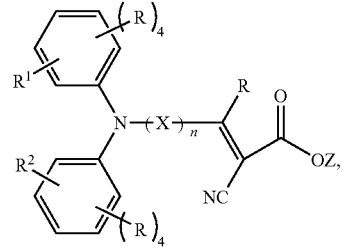

(I)

wherein: n is an integral of 2, 3, 4, 5, 6, 7, 8, 9, 10 or 11; the plurality of X is independent and elected from the group consisting of

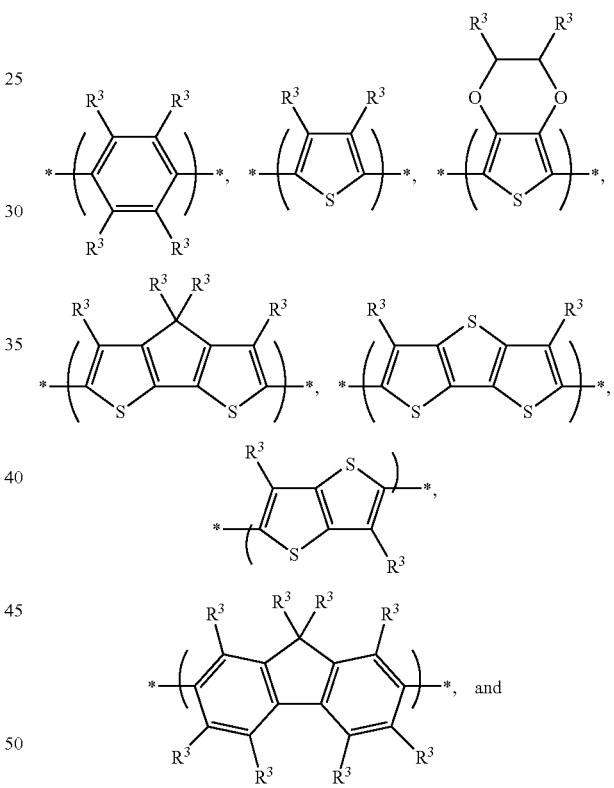

combinations thereof; R, $R^1$, and $R^2$ are independent and comprise hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group, or $R^1$ is connected to $R^2$ to form a ring having 5-14 members; $R^3$ is independent and comprise hydrogen, halogen, nitro group, amino group, $C_{1-18}$ alkyl group, $C_{1-18}$ alkoxy group, $C_{1-18}$ sulfanyl group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; and Z is hydrogen, alkali metal, or quaternary ammonium salt.

In another exemplary embodiment of the invention, an organic dye has a Formula (II), of:

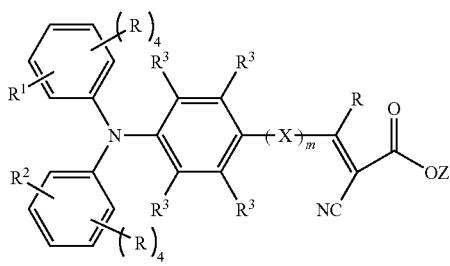

wherein, m is an integral of 1-10; the plurality of X is independent and elected from the group consisting of

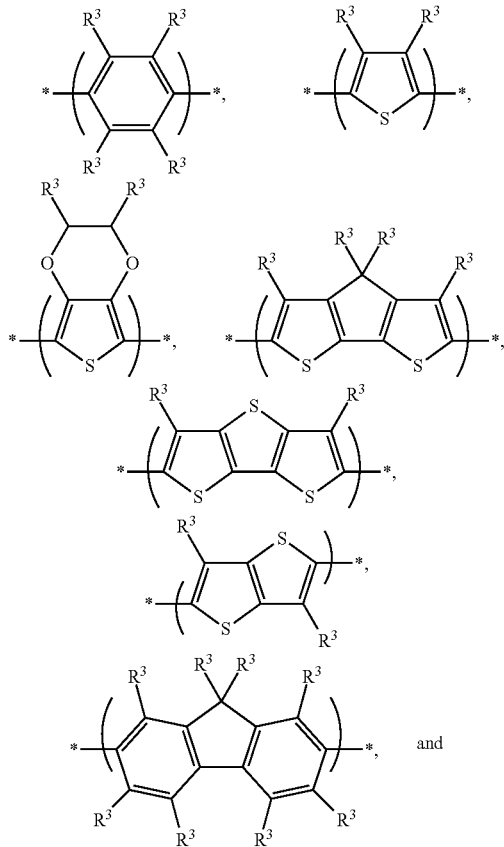

combinations thereof; R is independent and comprises hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; $R^1$ and $R^2$ are independent and comprise hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group, or $R^1$ is connected to $R^2$ to form a ring having 5-14 members; $R^3$ is independent and comprises hydrogen, halogen, nitro group, amino group, $C_{1-18}$ alkyl group, $C_{1-18}$ alkoxy group, $C_{1-18}$ sulfanyl group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; and Z is hydrogen, alkali metal (such as Li, Na, or K), or quaternary ammonium salt.

In yet another exemplary embodiment of the invention, an organic dye has a Formula (III), of:

wherein, i is 0 or an integral of 1-10; j is 0 or an integral of 1-10, and the sum of i and j is not more than 10; the plurality of X is independent and elected from the group consisting of and combinations thereof; R is independent and comprises hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; $R^1$ and $R^2$ are independent and comprise hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group, or $R^1$ is connected to $R^2$ to form a ring having 5-14 members; $R^3$ is independent and comprises hydrogen, halogen, nitro group, amino group, $C_{1-18}$ alkyl group, $C_{1-18}$ alkoxy group, $C_{1-18}$ sulfanyl group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; and Z is hydrogen, alkali metal, or quaternary ammonium salt.

Still another exemplary embodiment of the invention provides a photoelectric conversion device, wherein the photoelectric conversion device includes the aforementioned organic dyes. The photoelectric conversion devices include a flat display device, an organic electroluminescent device, an organicphotovoltaic device, or a solar cell (such as a dye-sensitized solar cell).

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein:

FIG. 1 shows a cross section of a dye-sensitized solar cell disclosed by an embodiment of the invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Preparation of Organic Dyes

The invention discloses organic dyes have an end of a diphenylamine moiety serving as a donor and another end of a CN—COOZ moiety (Z is hydrogen, alkali metal, or quaternary ammonium salt) serving as a acceptor, wherein the both ends are linked by a plurality of conjugated moiety, such as

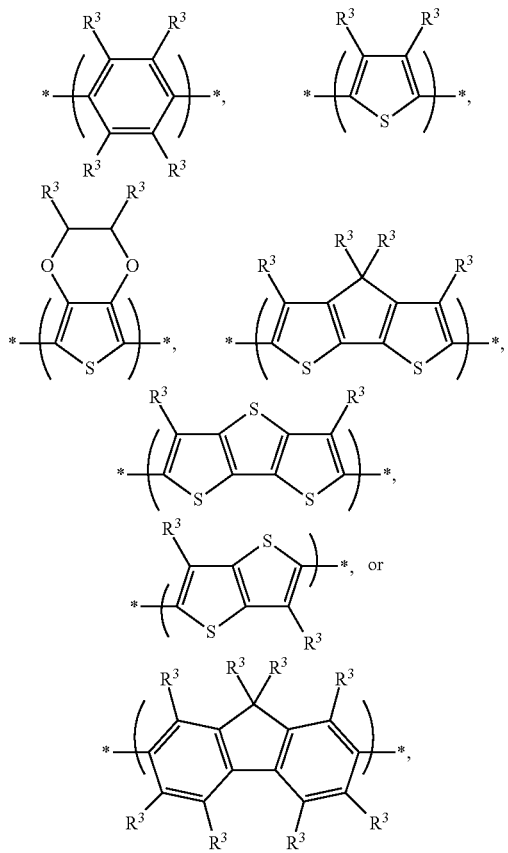

wherein $R^3$ is independent and comprise hydrogen, halogen, nitro group, amino group, $C_{1-18}$ alkyl group, $C_{1-18}$ alkoxy group, $C_{1-18}$ sulfanyl group, $C_{1-18}$ heteroalkyl group, $C_{3-20}$ aryl group, $C_{3-20}$ heteroaryl group, $C_{3-20}$ cycloaliphatic group or $C_{3-20}$ cycloalkyl group.

The organic dyes according to the invention have structures represented by Formulas (I), (II) and (III):

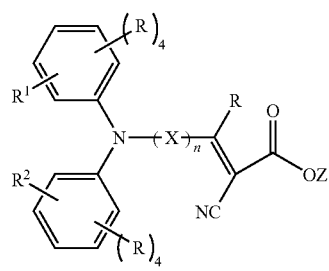

Formula (I)

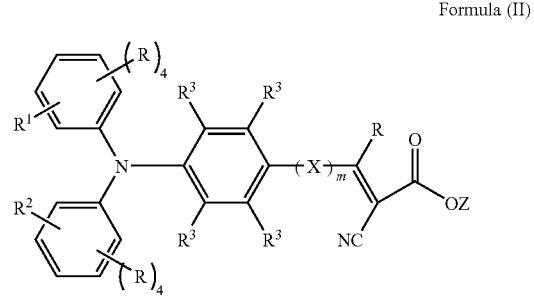

Formula (II)

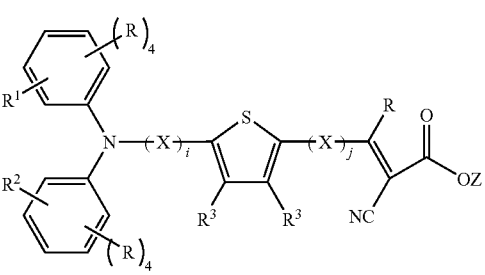

Formula (III)

wherein, n is an integral of 2-11; m is an integral of 1-10; i is 0 or an integral of 1-10; j is 0 or an integral of 1-10, and the sum of i and j is not more than 10; the plurality of X is independent and elected from the group consisting of

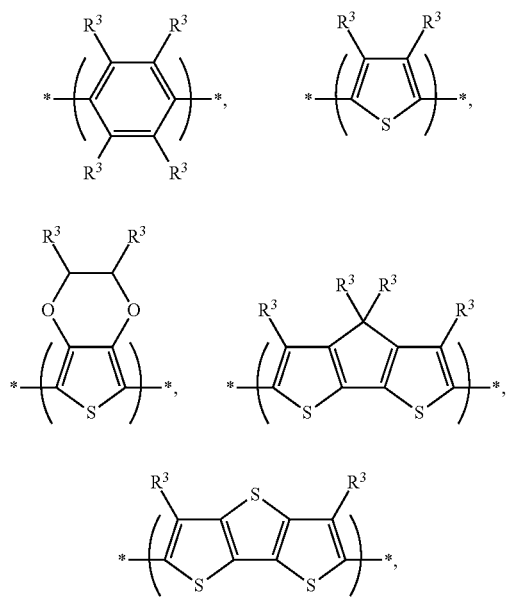

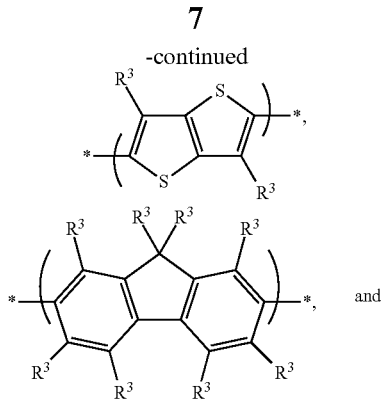

combinations thereof; R is independent and comprises hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; $R^1$ and $R^2$ are independent and comprise hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group, or $R^1$ is connected to $R^2$ to form a ring having 5-14 members; $R^3$ is independent and comprises hydrogen, halogen, nitro group, amino group, $C_{1-18}$ alkyl group, $C_{1-18}$ alkoxy group, $C_{1-18}$ sulfanyl group, $C_{3-18}$ heteroalkyl group, $C_{3-20}$ aryl group, $C_{3-20}$ heteroaryl group, $C_{3-20}$ cycloaliphatic group or $C_{3-20}$ cycloalkyl group; and Z is hydrogen, alkali metal, or quaternary ammonium salt.

The $C_{1-18}$ alkyl group includes (but is not limited to) methyl group, ethyl group, propyl group, iso-propyl group, butyl group, iso-butyl group, pentyl group, hexyl group, heptyl group, or octyl group. The $C_{1-18}$ alkoxy group includes (but is not limited to) methoxy group, ethoxy group, propoxy group, iso-propoxy group, butoxy group, iso-butoxy group, pentoxy group, hexoxy group, heptoxy group, or octoxy group. The $C_{3-20}$ aryl group, $C_{3-20}$ heteroaryl group, $C_{3-20}$ cycloaliphatic group, and $C_{3-20}$ cycloalkyl group include (but is not limited to) phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

The ring formed by connecting $R^1$, $R^2$, and benzene can be a fused moiety, such as

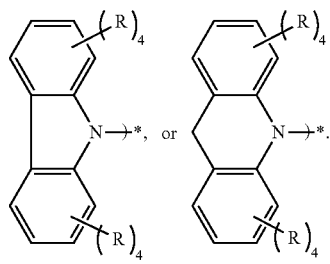

It should be noted that the organic dyes of the invention exhibit high absorption coefficients and modified energy gaps corresponding to the solar energy spectrum, thereby enhancing the photoelectric conversion efficiency of solar cells employing the organic dyes.

The chemical structures of the organic dyes according to embodiments of the invention are shown in Table 1.

TABLE 1

| Example No. | Chemical Structure |
| --- | --- |
| 1 | W-01 |
| 2 | W-02 |

TABLE 1-continued
| Example No. | Chemical Structure |
| --- | --- |
| 3 | 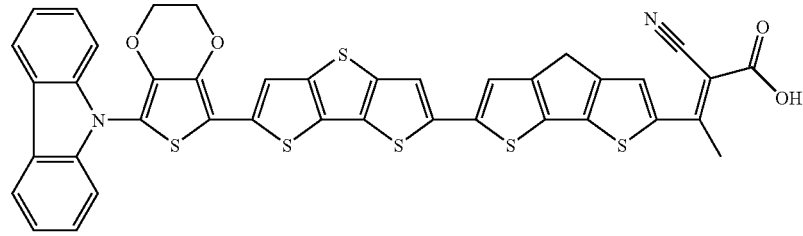<br>W-03 |
| 4 | 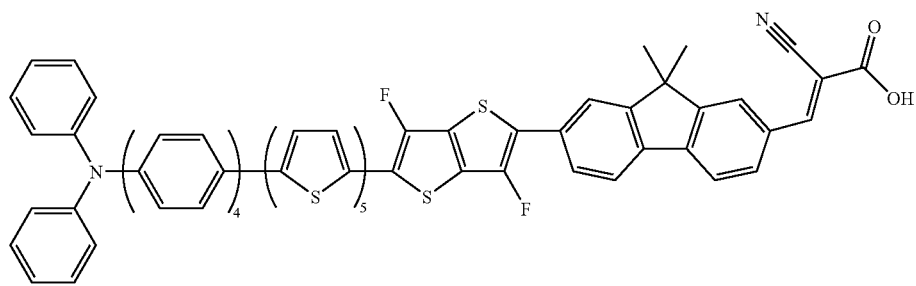<br>W-04 |
| 5 | 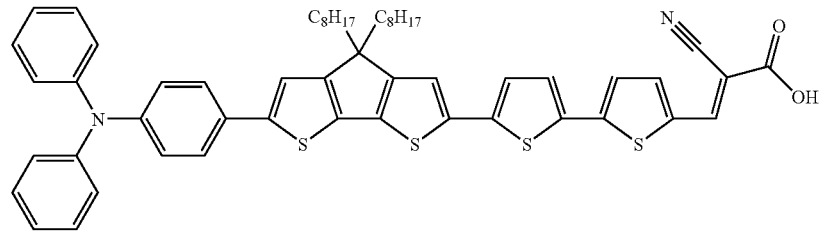<br>W-05 |
| 6 | 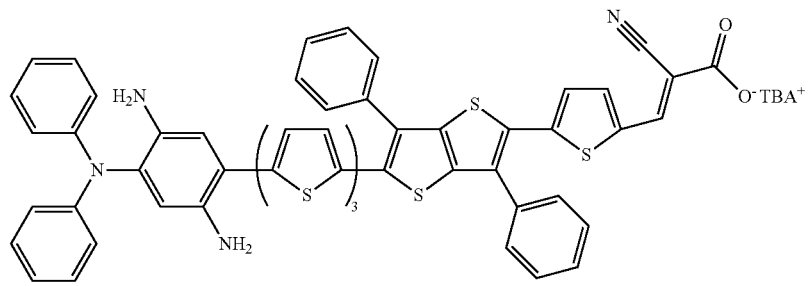<br>W-06 |

TABLE 1-continued
| Example No. | Chemical Structure |
|---|---|
| 7 | 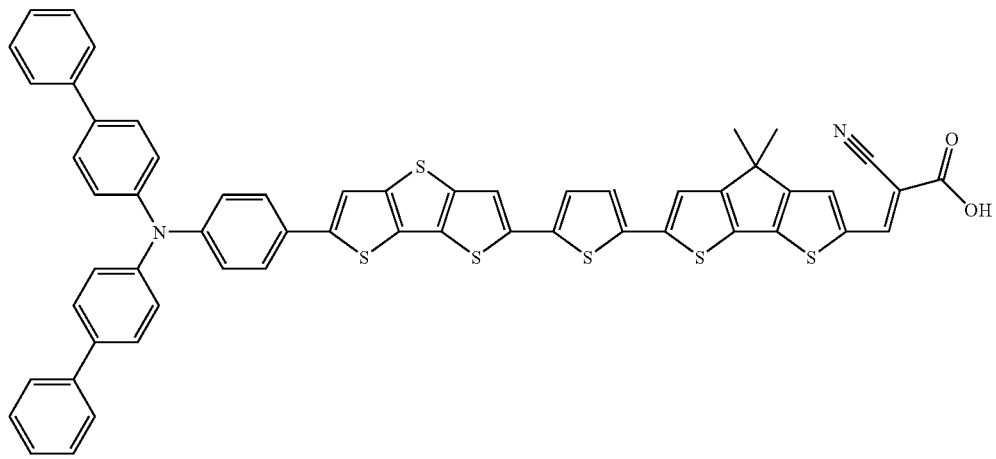<br>W-07 |
| 8 | 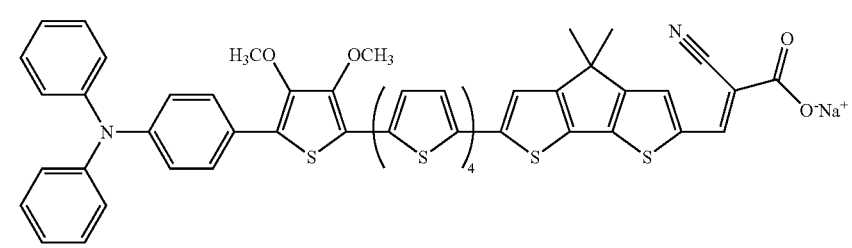<br>W-08 |
| 9 | 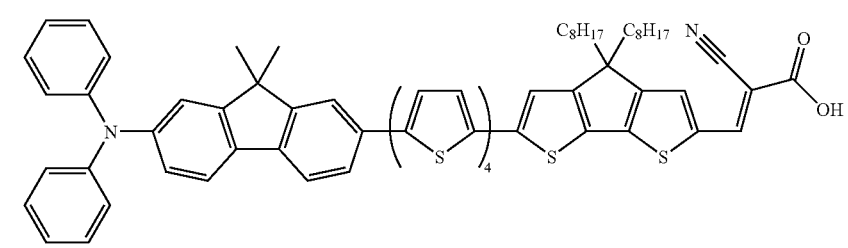<br>W-09 |
| 10 | 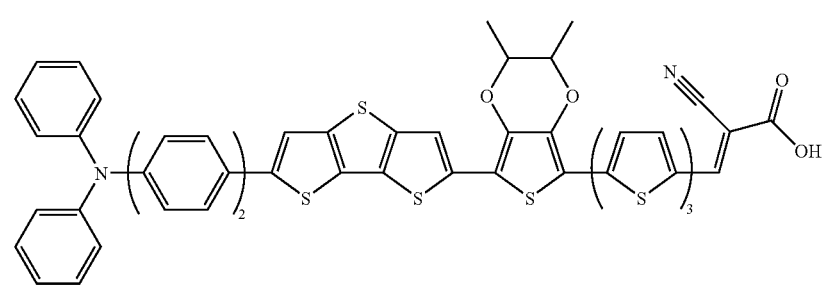<br>W-10 |

TABLE 1-continued

| Example No. | Chemical Structure |
|---|---|
| 11 | W-11 |
| 12 | W-12 |
| 13 | W-13 |
| 14 | W-14 |

TABLE 1-continued

| Example No. | Chemical Structure |
|---|---|
| 15 | 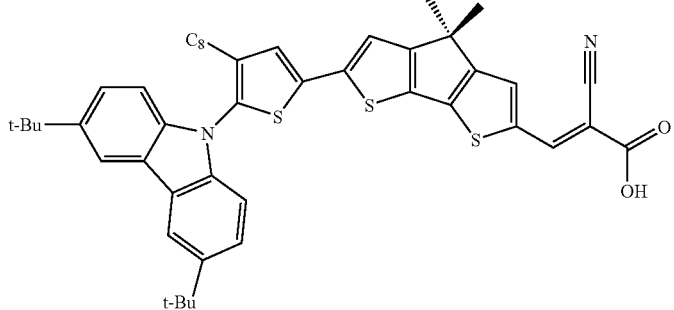
W-15 |
| 16 | 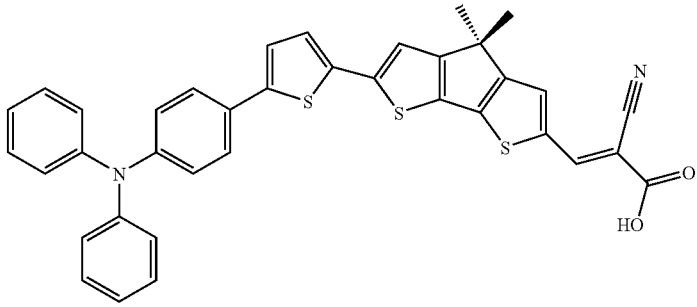
W-16 |

In order to clearly illustrate the method for preparing the organic dyes according to the invention, the preparation of compounds disclosed in Examples 1, and 5 are described in detail as below.

EXAMPLE 1

Preparation of compound W-01

First, 8 g of DOCPDT (4,4-Dioctyl-4H-cyclopenta[2,1-b;3,4-b']-dithiophene) was added into a 100 ml reaction bottle and dissolved using 50 ml of THF (tetrahydrofuran). Next, 7.95 ml of n-BuLi (n-butyl lithium) was added into the bottle at −78° C. After stirring for 2 hr, 4.36 g of Me$_3$SnCl (dissolved in 10 ml of THF) was added into the bottle. After reacting at −78° C. for 2 hr and at room temperature for 10 hr, water was added into the bottle to quench the reaction, and the mixture was extracted using CH$_2$Cl$_2$. An organic phase was separated and dried by MgSO$_4$. After filtrating, the filtrate was concentrated to remove the organic solvent, obtaining TMSn-CPDT (4,4-Dioctyl-2-trimethylstannanyl-4H-cyclo-penta[2,1-b;3,4-b']-dithiophene).

Next, 9.5 g of TMSn-CPDT(4,4-Dioctyl-2-trimethylstannanyl-4H-cyclo-penta[2,1-b;3,4-b']-dithiophene) and 5.43 g of (4-bromophenyl)-diphenyl-amine were added into a reaction bottle and dissolved with 100 ml of DMF (dimethylformamide). The mixture was cooled to −78° C. and heated to room temperature and filled and exhausted with Ar (four times). Next, 0.58 g of Pd(PPh$_3$)$_4$ (dissolved in 20 ml of DMF) was added into the bottle and heated to reflux for 24 hr. After cooling to room temperature, saturated NH$_4$Cl was added to quench the reaction. The result was extracted using CH$_2$Cl$_2$. An organic phase was separated and dried by MgSO$_4$. After filtrating, the filtrate was concentrated to remove the organic solvent, and CPDT-TPA([4-(4,4-Dioctyl-4H-cyclopenta-[2,1-b;3,4-b']dithiophen-2-yl)-phenyl]-diphenyl-amine) was obtained as an orange liquid.

Next, 5.8 g of CPDT-TPA([4-(4,4-Dioctyl-4H-cyclopenta-[2,1-b;3,4-b']dithiophen-2-yl)-phenyl]-diphenyl-amine) was added into a reaction bottle and dissolved in 100 ml of THF. Next, 4.31 ml of n-BuLi (n-butyl lithium) was added into the bottle at −78° C. After reacting for 1.5 hr, 2.33 g of Me$_3$SnCl (dissolved in 20 ml of THF) was added into the bottle. After reacting at −78° C. for 15 min and at room temperature for 10 hr, water was added into the bottle to quench reaction. The result was extracted using CH$_2$Cl$_2$. An organic phase was separated and dried by MgSO$_4$. After filtrating, the filtrate was concentrated to remove the organic solvent, obtaining TMSn-CPDT-TPA([4-(4,4-Dioctyl-6-trimethylatannanyl-4H-cyclopenta[2,1-b;3,4-b']dithiophen-2-yl)-phenyl]-diphenyl-amine).

Next, 1.21 g of Br-DMfluorene-aldehyde and 3.24 g of TMSn-CPDT-TPA([4-(4,4-Dioctyl-6-trimethylatannanyl-4H-cyclopenta[2,1-b;3,4-b']dithiophen-2-yl)-phenyl]-diphenyl-amine) were added into a reaction bottle and dissolved in 50 ml of DMF (dimethylformamide). The mixture was cooled to −78° C. and heated to room temperature and filled and exhausted with Ar (four times). Next, 0.14 g of Pd(PPh$_3$)$_4$ (dissolved in 20 ml of DMF) was added into the bottle and heated to reflux for 16 hr. After cooling to room temperature, saturated NH$_4$Cl was added to quench the reaction. The result was extracted using CH$_2$Cl$_2$. An organic phase was separated and dried by MgSO$_4$. After filtrating, the filtrate was concentrated to remove the organic solvent. After purification by column chromatography with n-hexane as the extraction solvent, F—Cl-aldehyde(7-[6-(4-diphenylamino-phenyl)-4,4-

Dioctyl-4H-cyclopenta-[2,1-b;3,4-b']dithiophen-2-yl]-9,9-dimethyl-9H-fluorene-2-carbaldehyde) was obtained as a red solid.

Next, 1 g of F—Cl-aldehyde(7-[6-(4-diphenylamino-phenyl)-4,4-Dioctyl-4H-cyclopenta-[2,1-b;3,4-b']dithiophen-2-yl]-9,9-dimethyl-9H-fluorene-2-carbaldehyde), 0.14 g of $NH_4OAc$, and 0.16 g of $CNCH_2COOH$ were added into a reaction bottle and dissolved in 50 ml of $CH_3COOH$. Next, the mixture was refluxed for 6 hr under Ar. After cooling to room temperature, the results were filtrated, extracted by $CH_2Cl_2$ and washed by water several times. Finally, the result was recrystallized from hexane. After centrifugal separation, the organic dye W-01 (2-cyano-3-{7-[6-(4-diphenylamino-phenyl)-4,4-Dioctyl-4H-cyclopenta-[2,1-b;3,4-b']dithiophen-2-yl]-9,9-dimethyl-9H-fluoren-2-yl}-acrylic acid) was obtained as a purple-black solid.

The synthesis pathway of the organic dye W-01 was as follows:

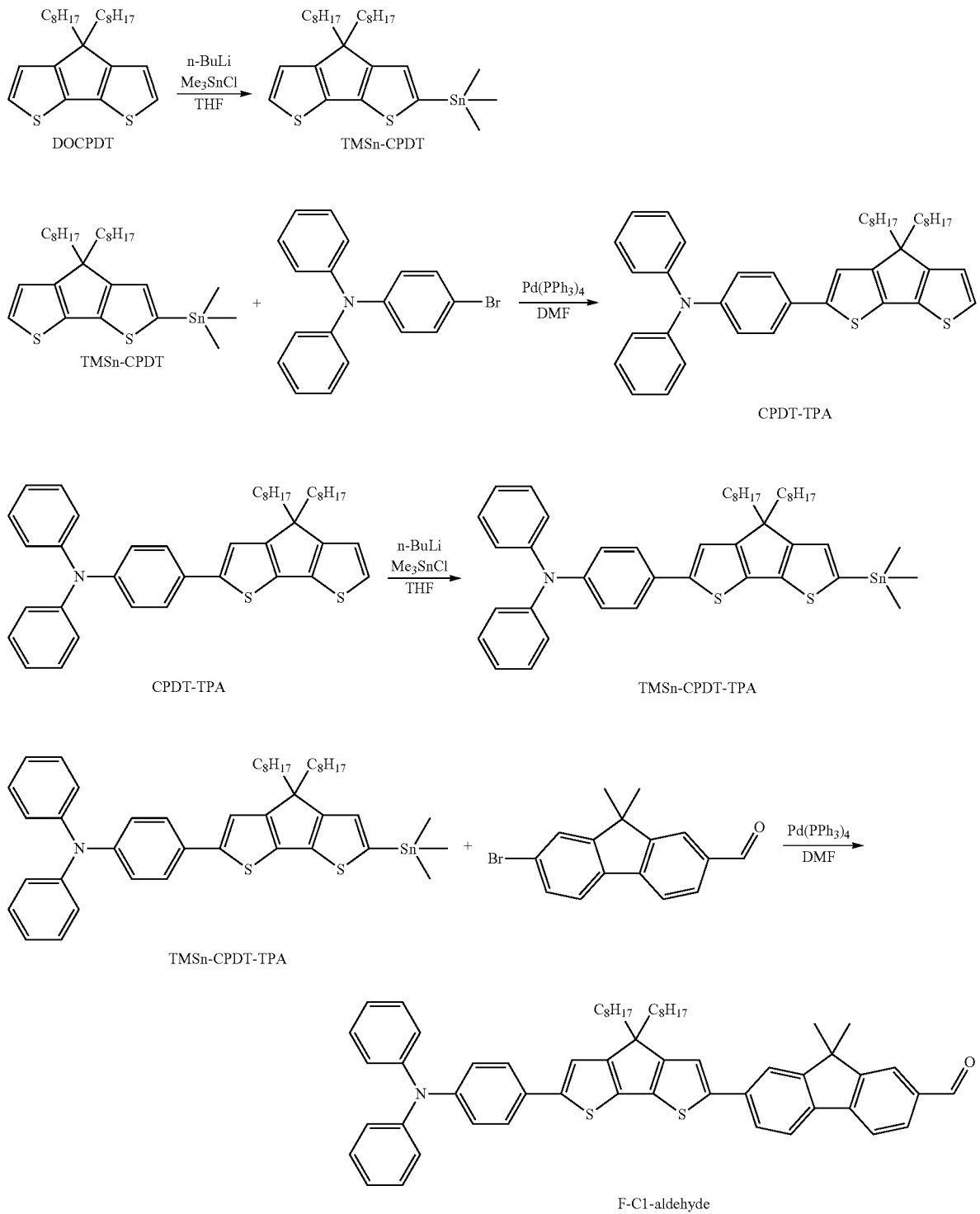

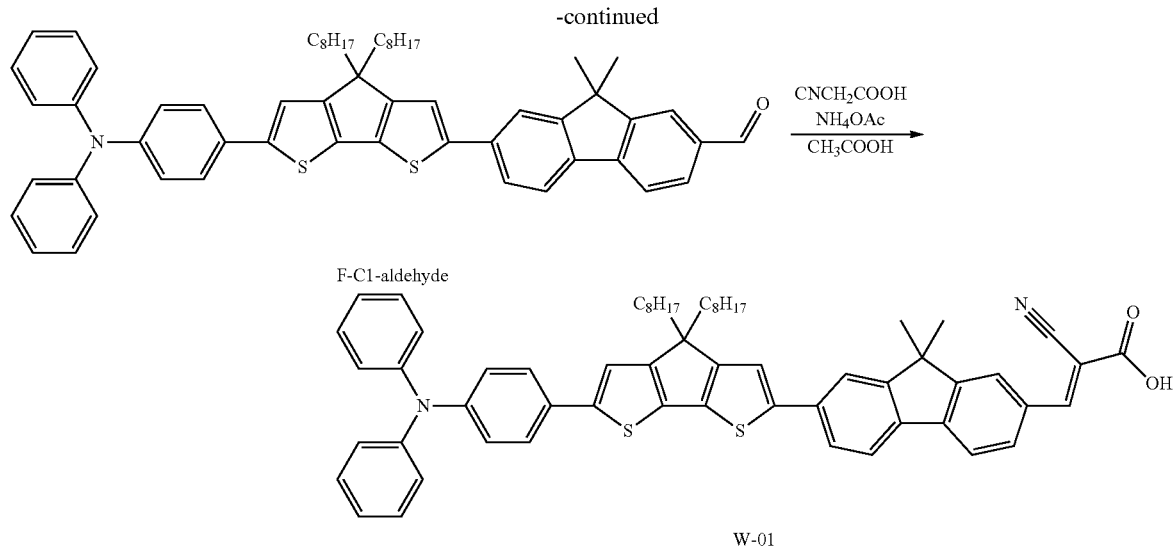

F-C1-aldehyde

W-01

EXAMPLE 5

Preparation of Compound W-05

First, 8 g of DOCPDT (4,4-Dioctyl-4H-cyclopenta[2,1-b; 3,4-b']-dithiophene) was added into a reaction bottle and dissolved using 50 ml of THF (tetrahydrofuran). Next, 7.95 ml of n-BuLi (n-butyl lithium) was added into the bottle at −78° C. After stirring for 2 hr, 4.36 g of $Me_3SnCl$ (dissolved in 10 ml of THF) was added into the bottle. After reacting at −78° C. for 2 hr and at room temperature for 10 hr, water was added into the bottle to quench the reaction, and the mixture was extracted using $CH_2Cl_2$. An organic phase was separated and dried by $MgSO_4$. After filtrating, the filtrate was concentrated to remove the organic solvent, obtaining TMSn-CPDT (4,4-Dioctyl-2-trimethylstannanyl-4H-cyclo-penta[2,1-b;3, 4-b']-dithiophene).

Next, 9.5 g of TMSn-CPDT(4,4-Dioctyl-2-trimethylstannanyl-4H-cyclo-penta[2,1-b;3,4-b']-dithiophene) and 5.43 g of (4-bromophenyl)-diphenyl-amine were added into a reaction bottle and dissolved using 100 ml of DMF (dimethylformamide). The mixture was cooled to −78° C. and heated to room temperature and filled and exhausted with Ar (four times). Next, 0.58 g of $Pd(PPh_3)_4$ (dissolved in 20 ml of DMF) was added into the bottle and heated to reflux for 24 hr. After cooling to room temperature, saturated $NH_4Cl$ was added to quench the reaction. The result was extracted using $CH_2Cl_2$. An organic phase was separated and dried by $MgSO_4$. After filtrating, the filtrate was concentrated to remove the organic solvent, and CPDT-TPA([4-(4,4-Dioctyl-4H-cyclopenta-[2, 1-b;3,4-b']dithiophen-2-yl)-phenyl]-diphenyl-amine) was obtained as an orange liquid.

Next, 5.8 g of CPDT-TPA([4-(4,4-Dioctyl-4H-cyclopenta-[2,1-b;3,4-b']dithiophen-2-yl)-phenyl]-diphenyl-amine) was added into a reaction bottle and dissolved in 100 ml of THF. Next, 4.31 ml of n-BuLi (n-butyl lithium) was added into the bottle at −78° C. After reacting for 1.5 hr, 2.33 g of $Me_3SnCl$ (dissolved in 20 ml of THF) was added into the bottle. After reacting at −78° C. for 15 min and at room temperature for 10 hr, water was added into the bottle to quench reaction. The result was extracted using $CH_2Cl_2$. An organic phase was separated and dried by $MgSO_4$. After filtrating, the filtrate was concentrated to remove the organic solvent, obtaining TMSn-CPDT-TPA([4-(4,4-Dioctyl-6-trimethylatannanyl-4H-cyclopenta[2,1-b;3,4-b']dithiophen-2-yl)-phenyl]-diphenyl-amine).

Next, 1.45 g of Br-Dithiphene-aldehyde and 4 g of TMSn-CPDT-TPA([4-(4,4-Dioctyl-6-trimethylatannanyl-4H-cyclopenta[2,1-b;3,4-b']dithiophen-2-yl)-phenyl]-diphenyl-amine) were added into a reaction bottle and dissolved in 50 ml of DMF (dimethylformamide). The mixture was cooled to −78° C. and heated to room temperature and filled and exhausted with Ar (four times). Next, 0.14 g of $Pd(PPh_3)_4$ (dissolved in 20 ml of DMF) was added into the bottle and heated to reflux for 16 hr. After cooling to room temperature, saturated $NH_4Cl$ was added to quench the reaction. The result was extracted using $CH_2Cl_2$. An organic phase was separated and dried by $MgSO_4$. After filtrating, the filtrate was concentrated to remove the organic solvent. After purification by column chromatography with n-hexane as the extraction solvent, F—C2-aldehyde(5'-[6-(4-diphenylamino-phenyl)-4,4-Dioctyl-4H-cyclopenta-[2,1-b;3,4-b']dithiophen-2-yl]-2,2'-bithiophenyl-5-carbaldehyde) was obtained as a red solid.

Next, 0.6 g of F—C2-aldehyde(7-[6-(4-diphenylamino-phenyl)-4,4-Dioctyl-4H-cyclopenta-[2,1-b;3,4-b'] dithiophen-2-yl]-9,9-dimethyl-9H-fluorene-2-carbaldehyde), 0.084 g g of $NH_4OAc$, and 0.092 g of $CNCH_2COOH$ were added into a reaction bottle and dissolved in 50 ml of $CH_3COOH$. Next, the mixture was refluxed for 6 hr under Ar. After cooling to room temperature, the results were filtrated, extracted by $CH_2Cl_2$ and washed by water several times. Finally, the result was recrystallized from hexane. After centrifugal separation, the organic dye W-05(2-cyano-3-{5'-[6-(4-diphenylamino-phenyl)-4,4-Dioctyl-4H-cyclopenta-[2,1-b;3,4-b']dithiophen-2-yl]-[2,2']bithiophenyl-5-yl}-acrylic acid) was obtained as a purple-black solid.

The synthesis pathway of the organic dye W-05 was as follows:

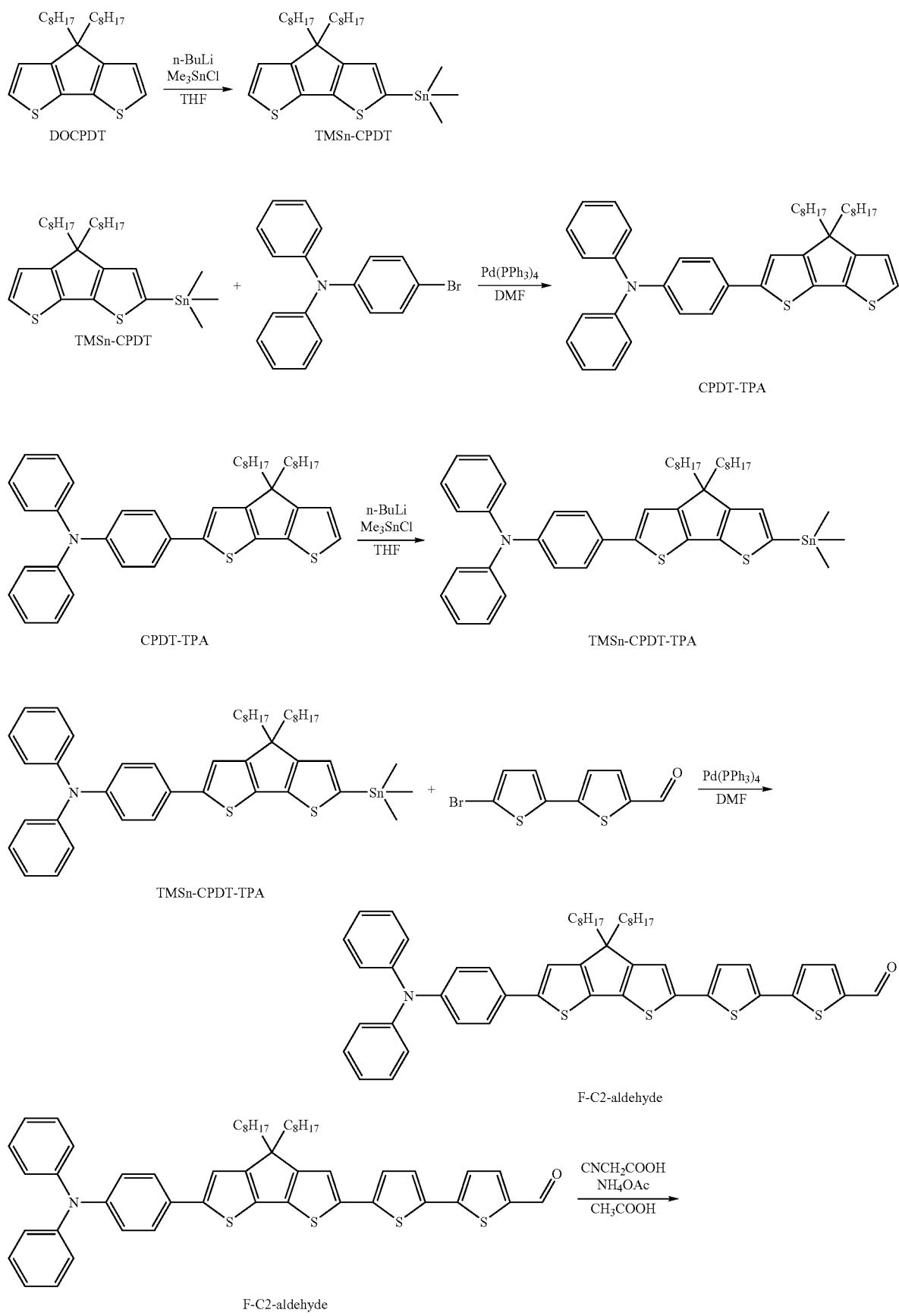

-continued

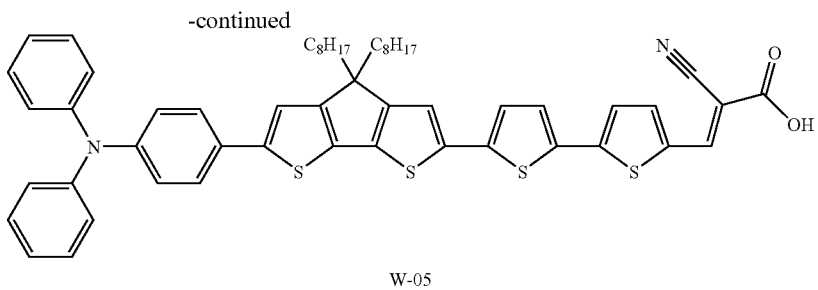

W-05

PREPARATION OF THE DYE-SENSITIZED SOLAR CELL

Example 11

The organic dye W-01 prepared in Example 1 was used for fabricating a dye-sensitized solar cell 100, as shown in FIG. 1. The fabricating method comprised the following steps:

First, a previously prepared working electrode 10 (including a transparent conductive substrate 12 and a porous $TiO_2$ layer 14) was immersed into a solution including the organic dye 16 (the organic dye W-01 prepared in Example 1) for several minutes. Herein, the organic dye 16 was adsorbed by the surfaces of the $TiO_2$ layer 14 via self-assembly. Next, the working electrode 10 was washed with a solvent. After drying, the working electrode 10 was encapsulated with a counter electrode 20 by an epoxy resin or a UV curing agent. Next, an electrolyte (0.5M LiI/0.05M $I_2$/0.5M TBP/Acetonitrile) was filled into the cell before sealing the opening, thus completing fabrication of the dye-sensitized solar cell A. Next, the voltage, current, and photoelectric conversion efficiency of the dye-sensitized solar cell A were measured and are shown in Table 2.

Example 12

First, a previously prepared working electrode 10 (including a transparent conductive substrate 12 and a porous $TiO_2$ layer 14) was immersed into a solution including the organic dye 16 (the organic dye W-05 prepared in Example 5) for several minutes. Herein, the organic dye 16 was adsorbed by the surfaces of the $TiO_2$ layer 14 via self-assembly. Next, the working electrode 10 was washed with a solvent. After drying, the working electrode 10 was encapsulated with a counter electrode 20 by an epoxy resin or a UV curing agent. Next, an electrolyte (0.5M LiI/0.05M $I_2$/0.5M TBP/Acetonitrile) was filled into the cell before sealing the opening, thus completing fabrication of the dye-sensitized solar cell B. Next, the voltage, current, and photoelectric conversion efficiency of the dye-sensitized solar cell B were measured and are shown in Table 2.

TABLE 2

| dye | principal absorption wavelength and principal absorption coefficient nm/(*$10^3 M^{-1} cm^{-1}$) | short-circuit current Isc(mA/cm$^2$) | open-circuit voltage Voc(V) | photoelectric conversion efficiency η(%) |
|---|---|---|---|---|
| W-01 | 411(76.2) | 11.40 | 0.66 | 4.62 |
| W-05 | 516(45.7) | 11.13 | 0.56 | 3.88 |

Examples 13-18

Examples 13-18 was performed as Example 11 except for the substitution of the organic dye W-01 respectively by the organic dyes W-11, W-12, W-13, W-14, W-15, and W-16 shown in Table 1. Next, the voltage, current, and photoelectric conversion efficiency of the obtained dye-sensitized solar cells were measured and are shown in Table 3.

TABLE 3

| dye | principal absorption wavelength and principal absorption coefficient nm/(*$10^3 M^{-1} cm^{-1}$) | short-circuit current Isc(mA/cm$^2$) | open-circuit voltage Voc(V) | photoelectric conversion efficiency η(%) |
|---|---|---|---|---|
| W-11 | 516(45.7) | 10.96 | 0.56 | 3.70 |
| W-12 | 478(76.9) | 11.83 | 0.60 | 4.10 |
| W-13 | 429(57.7) | 11.90 | 0.60 | 4.30 |
| W-14 | 445(65.6) | 12.05 | 0.59 | 4.50 |
| W-15 | 425(67.2) | 9.26 | 0.59 | 3.40 |
| W-16 | 506(47.1) | 14.11 | 0.59 | 5.00 |

The organic dyes of the invention exhibit high conjugation characteristics, lower LUMO energy levels, and reduced energy gaps. Therefore, the organic dyes can match the oxidation potential of an anode and the conductive energy gap of a cathode for a solar cell, thereby enhancing photoelectric conversion efficiency of a solar cell. Further, according to the organic dyes of the invention, the energy level of the excited state can match the conduction band energy level of metallic oxides (such as $TiO_2$) used in the solar cells, thereby promoting electron transport therein and reducing energy loss during electron transport. Moreover, the oxidation potential of the organic dyes of the invention is lower than that of the electrolyte (such as $I^-/I_3^-$) used in the solar cells, thus, allowing the electrons to be regained for organic dyes. Due to the polychromatic characteristics thereof, the organic dyes are suitable for and may be widely applied in photoelectric conversion devices.

While the invention has been described by way of example and in terms of embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic dye having a structure represented by

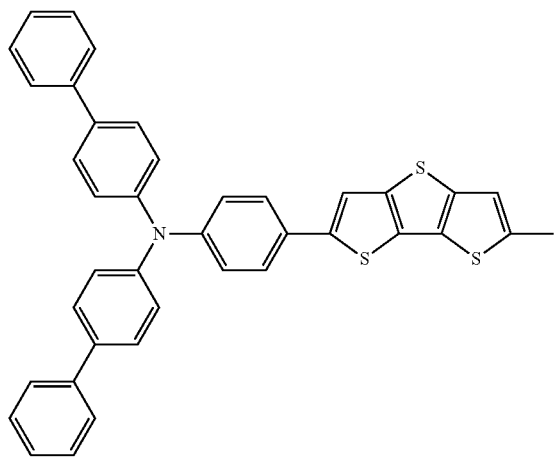

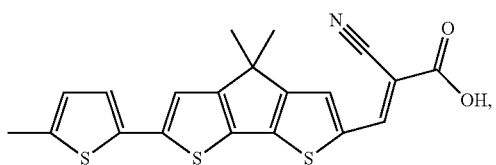

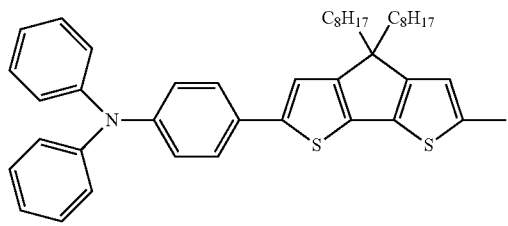

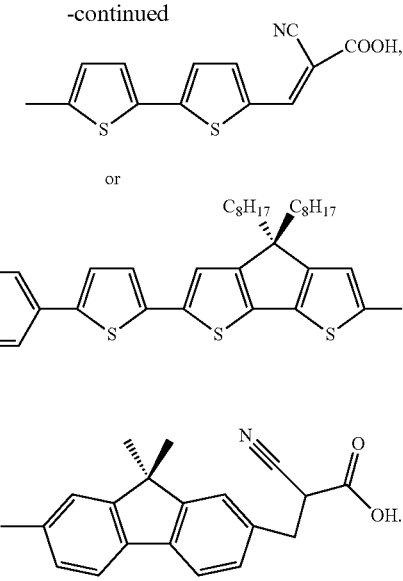

2. A photoelectric conversion device, comprising the organic dye as claimed in claim 1.

3. The photoelectric conversion device as claimed in claim 2, wherein the photoelectric conversion device comprises a flat display device.

4. The photoelectric conversion device as claimed in claim 2, wherein the photoelectric conversion device comprises an organic electroluminescent device.

5. The photoelectric conversion device as claimed in claim 2, wherein the photoelectric conversion device comprises an organicphotovoltaic device.

6. The photoelectric conversion device as claimed in claim 2, wherein the photoelectric conversion device comprises a solar cell.

7. The photoelectric conversion device as claimed in claim 2, wherein the photoelectric conversion device comprises a dye-sensitized solar cell.

* * * * *